United States Patent [19]

Bartlett et al.

[11] Patent Number: 5,371,099
[45] Date of Patent: Dec. 6, 1994

[54] PHENYL CARBOXAMIDE ISOXAZOLES

[75] Inventors: Robert R. Bartlett, Darmstadt, Germany; Matharu S. Singh, Cricklade; Elizabeth A. Kuo, Swindon, both of England; Rudolf Schleyerbach, Hofheim, Germany; Robert Westwood, Oxon, England

[73] Assignee: Roussel-Uclaf, France

[21] Appl. No.: 54,893

[22] Filed: Apr. 28, 1993

[30] Foreign Application Priority Data

Apr. 30, 1992 [GB] United Kingdom ............... 92-09330

[51] Int. Cl.$^5$ ............... C07D 261/08; C07D 261/12; A61K 31/42
[52] U.S. Cl. ..................................... 514/378; 548/248
[58] Field of Search .................... 548/248; 514/378

[56] References Cited

FOREIGN PATENT DOCUMENTS 0012435 6/1980 Germany ........................... 548/248

OTHER PUBLICATIONS

CA 115(15):159126k Preparation . . . immunomodulators. Patterson et al., p. 939, 1991.

Primary Examiner—Mary C. Lee
Assistant Examiner—Joseph K. McKane
Attorney, Agent, or Firm—Bierman and Muserlian

[57] ABSTRACT

A compound selected from the group consisting of a compound of the formula

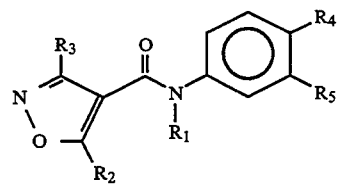

wherein $R_1$ is hydrogen or alkyl of 1 to 3 carbon atoms, $R_2$ is alkyl of 1 to 3 carbon atoms or cycloalkyl of 3 to 6 carbon atoms, $R_3$ is —COOR$_6$, R$_6$ is hydrogen or alkyl of 1 to 3 carbon atoms, $R_4$ is selected from the group consisting of halogen, —CN, —NO$_2$, —SCH$_3$, alkylcarbonyl of 1 to 6 alkyl carbon atoms, —CX$_3$, —WCX$_3$, —(CH$_2$)$_n$—CX$_3$, —(CX$_2$)$_n$—CX$_3$, —W—(CX$_2$)$_n$—CX$_3$, and —W—(CH$_2$)$_n$—CX$_3$, X is halogen, W is —O— or —S—, n is 1, 2 or 3, $R_5$ is selected from the group consisting of hydrogen, alkyl of 1 to 3 carbon atoms and cycloalkyl of 3 to 6 carbon atoms and their salts with non-toxic pharmaceutically acceptable bases with the proviso that if $R_2$ is alkyl of 1 to 3 carbon atoms, $R_1$ is hydrogen and $R_4$ is selected from the group consisting of halogen, —CX$_3$, —(CH$_2$)$_n$—CX$_3$, —(CX$_2$)$_n$—CX$_3$, —OCX$_3$, —O—(CH$_2$)$_n$—CX$_3$, and —O—(CH$_2$)$_n$—CX$_3$, X is halogen and n is 1, 2 or 3, $R_5$ cannot be hydrogen having anti-inflammatory activity and their preparation and intermediates.

12 Claims, 1 Drawing Sheet

FIG. 1A

HALF-LIFE APPROX. 37 HOURS

FIG. 1B

HALF-LIFE LESS THAN 4 HOURS

PHENYL CARBOXAMIDE ISOXAZOLES

OBJECTS OF THE INVENTION

It is an object of the invention to provide the novel compounds of formula I and their salts with non-toxic, pharmaceutically acceptable bases and a novel process and intermediates for their preparation.

It is another object of the invention to provide novel antiinflammatory compositions and a method of relieving inflammation in warm-blooded animals.

These and other objects and advantages of the invention will become obvious from the following detailed description.

BRIEF DESCRIPTION OF THE DRAWINGS

FIG. 1 graphically illustrates the kinetics of a known isoxazole carboxamide compound and a compound of the invention.

THE INVENTION

The novel compounds of the invention are selected from the group consisting of a compound of the formula wherein $R_1$ is hydrogen or alkyl of 1 to 3 carbon atoms, $R_2$ is alkyl of 1 to 3 carbon atoms or cycloalkyl of 3 to 6 carbon atoms, $R_3$ is —$COOR_6$, $R_6$ is hydrogen or alkyl of 1 to 3 carbon atoms, $R_4$ is selected from the group consisting of halogen, —CN, —$NO_2$, —$SCH_3$, alkylcarbonyl of 1 to 6 alkyl carbon atoms, —$CX_3$, —$WCX_3$, —$(CH_2)_n$—$CX_3$, —$(CX_2)_n$—$CX_3$, —W—$(CX_2)_n$—$CX_3$, and —W—$(CH_2)_n$—$CX_3$, X is halogen, W is —O— or —S—, n is 1, 2 or 3, $R_5$ is selected from the group consisting of hydrogen, alkyl of 1 to 3 carbon atoms and cycloalkyl of 3 to 6 carbon atoms and their salts with non-toxic pharmaceutically acceptable bases with the proviso that if $R_2$ is alkyl of 1 to 3 carbon atoms, $R_1$ is hydrogen and $R_4$ is selected from the group consisting of halogen, —$CX_3$, —$(CH_2)_n$—$CX_3$, —$(CX_2)_n$—$CX_3$, —$OCX_3$, —O—$(CX_2)_n$—$CX_3$, and —O—$(CH_2)_n$—$CX_3$, X is halogen and n is 1, 2 or 3, $R_5$ cannot be hydrogen having anti-inflammatory activity and their preparation and intermediates. The compounds include all tautomeric forms of the compounds of formula I.

Examples of cycloalkyl of 3 to 6 carbon atoms are cyclopropyl, cyclobutyl, cyclopentyl and cyclohexyl and examples of alkyl of 1 to 3 carbon atoms are methyl, ethyl, n-propyl and isopropyl. Examples of halogen are fluorine, chlorine, bromine and iodine.

Examples of non-toxic, pharmaceutically acceptable bases are inorganic or organic bases, such as sodium, potassium, lithium, calcium, magnesium and ammonium salts, or salts formed with organic bases such as methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine and N-methylglucamine.

Among the preferred compounds of formula I are those wherein $R_1$ is hydrogen, those wherein $R_2$ is methyl or cyclopropyl, those wherein $R_4$ is halogen, —CN, —$NO_2$, —$CF_3$, —$OCF_3$ or —$SCF_3$ and those wherein $R_5$ is hydrogen, methyl, ethyl or cyclopropyl. Most preferred are the compounds of formula I wherein $R_4$ is —$CF_3$, —$OCF_3$, or —$SCF_3$ and $R_5$ is a hydrogen or methyl.

Specific preferred compounds of formula I are:
5-methyl-4-[N-(3-methyl-4-trifluoromethyl)phenyl]-carbamoyl-3-isoxazolecarboxylic acid;
5-methyl-4-[N-(4-trifluoromethylthio)phenyl]carbamoyl-3-isoxazolecarboxylic acid;
5-methyl-4-[N-(3-methyl-4-trifluoromethoxy)-phenyl]-carbamoyl-3-isoxazolecarboxylic acid;
5-cyclopropyl-4-[N-(4-trifluoromethylthio)-phenyl]carbamoyl-3-isoxazolecarboxylic acid;
5-cyclopropyl-4-[N-(3-methyl-4-trifluoromethoxy)-phenyl]carbamoyl-3-isoxazolecarboxylic acid;
and the base addition salts thereof.

The novel process of the invention for the preparation of the compounds of formula I comprises reacting a compound of the formula wherein $R_1$, $R_2$, $R_4$ and $R_5$ are as defined above with a compound of the formula wherein Hal is halogen and $R_6$ is as defined above. The reaction is preferably effected in the presence of an anhydrous organic solvent such as dichloromethane or diethyl ether at low temperatures.

To prepare compounds of formula I wherein $R_3$ is —COOH, the compound formed by the reaction of the compounds of formulae II and III is saponified i.e. sulfuric acid in the presence of tetrahydrofuran and water or with lithium hydroxide in the presence of aqueous methanol.

The compounds of formula II may conveniently be prepared by reacting a compound of the formula wherein $R_1$, $R_2$, $R_4$ and $R_5$ are as defined above with pyrrolidine and may be subsequently reacted in situ without isolation with the compound of formula III. The reaction between the compound of formula IV and pyrrolidine is preferably effected in the presence of an anhydrous organic solvent such as benzene or ether and at reflux or at room temperature.

The compound of formula IV may be prepared by reacting a compound of the formula

V wherein $R_2$ is as defined above with a compound of the formula

VI wherein $R_1$, $R_4$ and $R_5$ are as defined above.

Alternatively, the compound of formula IV may be prepared by reacting a compound of the formula $R_2-COCH_2CO_2Et$     VII wherein $R_2$ is as defined above with a compound of formula VI as defined above.

The reaction between the compounds of formulae V or VII and the compound of formula VI is preferably effected in the presence of an anhydrous organic solvent such as xylene or toluene and with heat.

The compounds of formula VI are generally known products or can be prepared by diazotisation, then reduction of the corresponding nitroanilines by processes known per se. The nitroanilines can be prepared as indicated, for example, in TP, Sura et al. Synthetic communications (1988), Vol. 18 (16–17), p. 2161–5. Certain of the anilines of formula VI can be prepared by processes described in European Patent EP. 206,951 or by reduction of the corresponding nitrobenzenes.

The compounds of formula I are acidic in character when $R_3$ is $CO_2H$ and the base addition salts of the compounds of formula I can advantageously be prepared by reacting in approximately stoichiometric proportions an inorganic or organic base with the compound of formula I. The salts can be prepared without intermediate isolation of the corresponding compound.

The novel antiinflammatory compositions of the invention are comprised of an antiinflammatorily effective amount of at least one compound of formula I and its salts with non-toxic, pharmaceutically acceptable bases and an inert carrier. The compositions may be in the form of tablets, drages, capsules, granules, suppositories and injectable solutions.

Examples of inert pharmaceutical carriers are talc, gum arabic, starch, lactose, magnesium stearate, cocoa butter, aqueous or non-aqueous vehicles, fatty substances of animal or vegetable origin, paraffin derivatives, glycols, various wetting, dispersing or emulsifying agents and preservatives.

The compositions of the invention have remarkable antiinflammatory activity. They inhibit both the inflammatory response caused by irritant agents, and delayed hypersensitivity reactions by hindering activation of the immune cells by a specific antigen. They are useful in the treatment of rheumatoid arthritis and chronic inflammatory diseases of immune or non-immune origin i.e. graft vs. host disease, transplantation reactions, uveitis, psoriasis or cancer.

The novel method of invention for treating inflammation in warm-blooded animals, including humans, comprises administering to warm-blooded animals an antiinflammatorily effective amount of at least one compound of formula I and their salts with bases. The compounds may be administered orally, rectally or parenterally and the usual daily dose is 0.0013 to 2.66 mg/kg depending on the condition treated, the specific compound and the method of administration.

The compounds of formulae II and IV are novel.

In the following examples, there are described several preferred embodiments to illustrate the invention. However, it should be understood that the invention is not intended to be limited to the specific embodiments.

EXAMPLES

Example 1

5-methyl-4-[N-(4-nitrophenyl)]carbamoyl-3-isoxazolecarboxylic acid;

Step A

N-(4-nitrophenyl)-3-oxobutanamide 13.8 g (0.1 mol) of 4-nitroaniline were suspended in 20 ml of dry xylene and 14,22 g (0.1 mol) of 2,2,6-trimethyl-4H-1,3-dioxin-4-one were added. The reaction mixture was heated in an oil-bath at 150° C. for 30 minutes while the acetone formed in the reaction was removed by distillation. The reaction mixture was cooled to room temperature, filtered and the residue was washed thoroughly with ethyl acetate. The filtrate was evaporated to obtain 11.65 g (52%) of N-(4-nitrophenyl)-3-oxobutanamide as a white crystalline solid melting at 119°–21° C. (from ethyl acetate-petroleum ether (40°–60° C.)) (lit.* melting at 120°–122° C.).

* R. J. Clemens and J. A. Hyatt JOC; 50,2431–35(1985).

Step B

N-(4-nitrophenyl)-3-pyrrolidyl-2-butenamide

A mixture of 11.10 g (50 mmol) of N-(4-nitrophenyl)-3-oxobutanamide and 4.26 g (60 mmol) of pyrrolidine in 125 ml of benzene was refluxed for one hour using a Dean-Stark trap to separate water. The reaction was cooled to give 12.89 g (94% yield) of N-(4-nitrophenyl)-3-pyrrolidyl-2-butenamide as a yellow solid.

Step C ethyl 5-methyl-4-[N-(4-nitrophenyl)]carbamoyl-3-isoxazolecarboxylate (Example 14)

A suspension of 12.38 g (45 mmol) of the crude N-(4-nitrophenyl)-3-pyrrolidyl-2-butenamide in 200 ml of dry dichloromethane was cooled to 0° C. and 7.50 g (49.5 mmol) of ethyl chlorooximidoacetate were added in one portion. The reaction mixture was stirred at −5° C. to 0° C. for 2 hours and was then poured into 200 ml of water. The aqueous layer was extracted with 100 ml of dichloromethane and the combined organic extract was washed with 100 ml of 10% HCl, 5% NaHCO$_3$ solution and then dried over MgSO$_4$. Evaporation of the solvent gave 10.91 g (76%) of ethyl 5-methyl-4-[N-(4-nitrophenyl)]carbamoyl-3-isoxazolecarboxylate as a white crystalline solid melting at 151°–53° C. (from ethyl acetate);

IR (KBr); 3120, 1700, 1670, 1620, 1580, 1505, 1335, 1215, 1025, 850 and 750 cm$^{-1}$; NMR (CDCl$_3$) δ 11.62(1H,s, —NH), 8.24 (2H,dd,J=2.2 Hz and 7.2 Hz, ArH), 7.88 (2H, dd, J=2.2 Hz and 7.2 Hz, ArH), 4.61

(2H,q,J=7.2 Hz,—CH$_2$) 2.89 (3H,s, —CH$_3$), 1.53 (3H,t,J=7.2 Hz, —CH$_2$CH$_3$).

Step D
5-methyl-4-[N-(4-nitrophenyl)]carbamoyl-3-isoxazolecarboxylic acid

A stirred solution of 7.98 g (25 mmol) of ethyl 5-methyl-4-[N-(4-nitrophenyl)carbamoyl-3-isoxazolecarboxylate in 125 ml of THF was treated with a solution of 7.5 ml of conc. H$_2$SO$_4$ in 50 ml of water. The solution was heated at 50° C. for 48 hours and was then cooled. Evaporation of the THF under reduced pressure gave 4.58 g (63%) of 5-methyl-4-[N-(4-nitrophenyl)]carbamoyl-3-isoxazolecarboxylic acid as a white crystalline solid, melting at 260°-1° C.(dec.) (from ethyl acetate);
IR (KBr); 3600–2700, 1715, 1675, 1625, 1575, 1505, 1335 and 1105 cm$^{-1}$; NMR (DMSO-d$_6$); δ 11.45 (1H,s,—NH), 8.33 (2H, dd, J=2 Hz and 9.2 Hz, ArH), 7.92 (2H, dd, J=2 Hz and 9.2 Hz, ArH), 6.50–4.00 (1H, bs, —CO$_2$H), 2.67 (3H,s, —CH$_3$).

Using the procedure of Example 1, the following compounds were prepared:

Example 2

4-[N-(4-cyanophenyl)]carbamoyl-5-methyl-3-isoxazolecarboxylic acid;

Example 3

4-[N-(4-bromo-3-methyl)phenyl]carbamoyl-5-methyl-3-isoxazolecarboxylic acid;

Example 4

4-[N-(4-chloro-3-methyl)phenyl]carbamoyl-5-methyl-3-isoxazolecarboxylic acid;

Example 5

5-methyl-4-[N-(3-methyl-4-trifluoromethyl)phenyl]carbamoyl-3-isoxazolecarboxylic acid;

Example 6

4-[N-(4-cyano-3-methyl)phenyl]carbamoyl-5-methyl-3-isoxazolecarboxylic acid;

Example 7

5-methyl-4-[N-(4-trifluoromethylthio)phenyl]carbamoyl-3-isoxazolecarboxylic acid;

Step A
N-[4-(trifluoromethylthio)phenyl]-3-oxobutanamide

A mixture of 7.72 g (40 mmol of 4-(trifluoromethylthio)aniline and 5.2 g (40 mmol) of ethyl acetoacetate in 80 ml of dry toluene was refluxed for 8 hours using a Dean-Stark trap to remove the ethanol formed during the reaction. The reaction mixture was cooled in an ice-bath to obtain 10.48 g (95%) of N-[4-(trifluoromethylthio)phenyl]-3-oxobutanamide as a white crystalline solid, melting at 120°-2° C.

Step B
3-pyrrolidyl-N-[4-(trifluoromethylthio)phenyl]-2-butenamide

A mixture of 11.08 g (40 mmol) of N-[4-(trifluoromethylthio)phenyl]-3-oxobutanamide and 3.41 g (48 mmol) of pyrrolidine in 100 ml of benzene was refluxed for 1 hour using a Dean-Stark trap to separate water. The reaction mixture was cooled in an ice-bath to obtain 12.57 g (95%) of 3-pyrrolidyl-[N-(4-trifluoromethylthio)phenyl]-2-butenamide as a white crystalline solid.

Step C
ethyl 5-methyl-4-[N-(4-trifluoromethylthio)phenyl]carbamoyl-3-isoxazolecarboxylate (Example 20)

A suspension of 11.55 g (35 mmol) of crude 3-pyrrolidyl-N-[4-(trifluoromethylthio)phenyl]-2-butenamide in 150 ml of dry dichloromethane was cooled to 0° C. and 6.67 g (44 mmol) of ethyl chlorooximidoacetate were added. The reaction was stirred at 0° C. for 2 hours and then was poured into 200 ml of water. The organic layer was separated and the aqueous layer was extracted with 100 ml of dichloromethane. The combined organic extracts were washed with 100 ml of 10% HCl, 50 ml of 5% NaHCO$_3$ solution and then dried over MgSO$_4$. Evaporation of the solvent yielded 9.74 g (74%) of ethyl 5-methyl-4-[N-(4-trifluoromethylthio)phenyl]carbamoyl-3-isoxazolecarboxylate as a white crystalline solid, melting at 117°-8° C. (from ether/petroleum ether (40°-60°),
IR (KBr); 3120, 1710, 1680, 1615, 1325, 1210 and 1135 cm$^{-1}$; NMR (CDCl$_3$) δ 11.32 (1H,s,—NH), 7.79 (2H,d, J=8.8 Hz, ArH), 7.64(2H,d,J=8.8 Hz, ArH), 4.59 (2H, q, J=7.2 Hz, —CH$_2$), 2.88 (3H, s, —CH$_3$), 1.51 (3H,t, J=7.2 Hz, —CH$_2$CH$_3$).

Step D
5-methyl-4-[N-(4-trifluoromethylthio)phenyl]carbamoyl-3-isoxazolecarboxylic acid A solution of 1.85 g (44 mmol ) of lithium hydroxide monohydrate in 25 ml of water was diluted with 250 ml of methanol and cooled to −15° C. 7.48 g (20 mmol) of ethyl 5-methyl-4-[N-(4-trifluoromethylthio)phenyl]carbamoyl-3-isoxazolecarboxylate were added in small portions to the lithium hydroxide solution and the resulting mixture was stirred at −15° C. for 5 hours, during which time 75 ml of water were added in small portions. The reaction mixture was filtered and the filtrate was diluted with 400 ml of water and acidified with 2N HCl to give 6.73 g (97%) of 5-methyl-4-[N-(4-trifluoromethylthio)-phenyl]carbamoyl-3-isoxazolecarboxylic acid as a white solid, melting at 158°-9° C. (dec.) (from ether/petroleum ether (40°-60°);
IR (KBr); 3600–2400, 1720, 1680, 1620, 1135 and 1110 cm$^{-1}$; NMR (DMSO-d$_6$); δ 11.08 (1H,s,—NH), 7.84 (1H,d,J=8.6 Hz, ArH), 7.76 (1H,d, J=8.6 Hz, ArH), 2.66 (3H,s, —CH$_3$).

Using the procedure of Example 7, the following compound was prepared:

Example 8

5-methyl-4-[N-(3-methyl-4-trifluoromethoxy)phenyl]carbamoyl-3-isoxazolecarboxylic acid;

Example 9

5-cyclopropyl-4-[N-(4-trifluoromethyl)phenyl]carbamoyl-3-isoxazolecarboxylic acid;

Step A
3-cyclopropyl-3-oxo-N-[4-(trifluoromethyl)phenyl]-propanamide

A mixture of 10.14 g (65 mmol) of ethyl 3-cyclopropyl-3-oxopropanoate and 10.47 g (65 mmol) of 4-aminobenzotrifluoride in 100 ml of dry toluene was refluxed for 8 hours using a Dean-Stark condenser to remove the ethanol formed during the reaction. The reaction mixture was cooled and petroleum ether (b.p. 40°-60° C.) was added to obtain 16.44 g (93%) of 3-cyclopropyl-3-oxo-N-[4-(trifluoromethyl)phenyl]-propanamide as a white crystalline solid, melting at 131°-2° C.

Step B
ethyl 5-cyclopropyl-4-[N-(4-trifluoromethyl)phenyl]carbamoyl-3-isoxazolecarboxylate (Example 22)

A mixture of 13.55 g (50 mmol) of 3-cyclopropyl-3-oxo-N-[4-(trifluoromethyl)phenyl]propanamide, 6.5 g of fused granular calcium chloride (8–16 mesh); and 3.55 g (50 mmol) of dry pyrrolidine in 350 ml of dry ether was stirred at room temperature for 3 hours. The 3-cyclopropyl-3-pyrrolidyl-N-[(4-trifluoromethyl)-phenyl]-2-propanamide was not isolated but subsequently reacted in situ. The reaction mixture was cooled to 0° C. and 11.37 g (75 mmol) of ethyl chlorooximidoacetate were added in one portion followed by 7.58 g (75 mmol) of dry triethylamine in 10 ml of dry ether added dropwise over 10 minutes. The mixture was stirred at 0° C. for 2 hours and then warmed to room temperature. After stirring for 30 minutes, the reaction mixture was poured into 200 ml of water and the organic layer was separated. The aqueous layer was extracted with 100 ml of ether and the combined organic extracts were washed with 100 ml of 10% HCl, 100 ml of 5% $NaHCO_3$ solution and dried over $MgSO_4$ and finally evaporated to dryness. Purification of the residue by flash chromatography (Kieselgel 60H, 120 g; $CH_2Cl_2$) yielded, 12.54 g (68%) of ethyl 5-cyclopropyl-4-[N-(4-trifluoromethyl)-phenyl]carbamoyl-3-isoxazolecarboxylate as a white crystalline solid, melting at 100°–1° C. (from petroleum ether (40°–60° C.);

IR (KBr); 3090, 1710, 1670, 1605, 1325, 1110 and 845 cm$^{-1}$; NMR $CDCl_3$; δ 11.31 (1H,s,—NH), 7.85 (2H, d, J=8.6 Hz, ArH), 7.61 (2H, d, J=8.6 Hz, ArH), 4.57 (2H,q, J=7.1 Hz, —$CH_2$), 3.38–3.24 (1H, m, cyclopropyl-H), 1.50 (3H, t, J=7.1 Hz, —$CH_3$), 1.40–1.23 (4H, m, cyclopropyl-H).

Step C 5-cyclopropyl-4-[N-(4-trifluoromethyl)phenyl]carbamoyl-3-isoxazolecarboxylic acid A solution of 2.14 g (51 mmol) of lithium hydroxide monohydrate in 25 ml of water was diluted with 75 ml of methanol and cooled to −15° C. A solution of 8.46 g (23 mmol) of ethyl 5-cyclopropyl-4-[N-(4-trifluoromethyl)phenyl]carbamoyl-3-isoxazolecarboxylate in 200 ml of methanol was added over 20 minutes to the lithium hydroxide solution and the resulting mixture was stirred at −20° C. to −15° C. for 1 hour. The mixture was filtered and the filtrate was diluted with 400 ml of water and acidified using 2N HCl to obtain 6.89 g (88%) of 5-cyclopropyl-4-[N-(4-trifluoromethyl)phenyl]carbamoyl-3-isoxazolecarboxylic acid as a white solid, melting at 160°–1° C. (dec.) (from ether/petroleum ether (40°–60 °);

IR (KBr); 3600–2300, 1715, 1635, 1600, 1565, 1325 and 1120 cm$^{-1}$; NMR (DMSO-$d_6$); δ 11.13 (1H,s, —NH), 7.90 (2H, d, J=8.6 Hz, ArH), 7.78 (2H, d, J=8.6 Hz, ArH), 2.60–2.49 (1H, m, cyclopropyl-H), 1.31–1.13 (4H, m, cyclopropyl-H).

Using the procedure of Example 9, the following compounds were prepared:

Example 10

5-cyclopropyl-4-[N-(3-methyl-4-trifluoromethyl)-phenyl]carbamoyl-3-isoxazolecarboxylic acid;

Example 11

5-cyclopropyl-4-[N-4-trifluoromethoxy)phenyl]carbamoyl-3-isoxazolecarboxylic acid;

Example 12

5-cyclopropyl-4-[N-(4-trifluoromethylthio)phenyl]carbamoyl-3-isoxazolecarboxylic acid;

Example 13

5-cyclopropyl-4-[N-(3-methyl-4-trifluoromethoxy)-phenyl]carbamoyl-3-isoxazolecarboxylic acid;

Using the procedure of Example 1, step C (example 14), the ethyl esters of the compounds of examples 2 to 6 were prepared.

Example 15

Ethyl-4-[N-(4-cyanophenyl)]carbamoyl-5-methyl-3-isoxazolecarboxylate.

Example 16

Ethyl-4-[N-(4-bromo-3-methyl)phenyl]carbamoyl-5-methyl-3-isoxazolecarboxylate.

Example 17

Ethyl-4-[N-(4-chloro-3-methyl)phenyl]carbamoyl-5-methyl-3-isoxazolecarboxylate.

Example 18

Ethyl 5-methyl-4-[N-(3-methyl-4-trifluoromethyl)-phenyl]carbamoyl-3-isoxazolecarboxylate.

Example 19

Ethyl 4-[N-(4-cyano-3-methyl)phenyl]carbamoyl-5-methyl-3-isoxazolecarboxylate.

Using the procedure of Example 7, step C, (example 20) the ethyl ester of the compound of example 8 was prepared.

Example 21

Ethyl 5-methyl-4-[N-(4-trifluoromethoxy)phenyl]carbamoyl-3-isoxazolecarboxylate.

Using the procedure of Example 9, step B, (example 22) the ethyl esters of the compounds 10 to 13 were prepared.

Example 23

Ethyl 5-cyclopropyl-4-[N-(3-methyl-4-trifluoromethyl)phenyl]carbamoyl-3-isoxazolecarboxylate.

Example 24

Ethyl 5-cyclopropyl-4-[N-(4-trifluoromethoxy)phenyl]-carbamoyl-3-isoxazolecarboxylate.

Example 25

Ethyl 5-cyclopropyl-4-[N-(4-trifluoromethylthio)-phenyl]carbamoyl-3-isoxazolecarboxylate.

Example 26

Ethyl 5-cyclopropyl-4-[N-(3-methyl-4-trifluoromethoxy)-phenyl]carbamoyl-3-isoxazolecarboxylate. Spectral data, yields, melting points, and analytical data for Examples 1 to 26 are given in Table I.

Example 27

Tablets were prepared containing 20 mg of the compound of Example 1 and sufficient excipient of lactose, starch, talc and magnesium stearate to prepare 150 mg tablets.

TABLE I

| Example | R4 | R5 | Synthetic Method | Yield (%) | Recryst. solvent | IR(KBr) $\nu_{max}$ cm$^{-1}$ | m.p. (°C.) | Formula | M.W. | C | H | N | X |
|---|---|---|---|---|---|---|---|---|---|---|---|---|---|
| | | | | | | | | | | \multicolumn{4}{c}{ANALYSIS Calculated/Found} | | | |

Structure for Examples 1–8:

HO$_2$C—[isoxazole with N-O, CH$_3$]—C(=O)—NH—C$_6$H$_3$(R$_4$)(R$_5$)

| Example | R4 | R5 | Synthetic Method | Yield (%) | Recryst. solvent | IR(KBr) $\nu_{max}$ cm$^{-1}$ | m.p. (°C.) | Formula | M.W. | C | H | N | X |
|---|---|---|---|---|---|---|---|---|---|---|---|---|---|
| 1 | NO$_2$ | H | 1 | 63 | EtOAc | 3600–2700, 1715,1675, 1625,1575, 1505,1335, 1105. | 260-1 (dec.) | C$_{12}$H$_9$N$_3$O$_6$ | 291.22 | 48.01 48.01 | 3.36 3.32 | 14.00 14.00 | —* — |
| 2 | CN | H | 1 | 62 | EtOAc | 3600–2300, 2240,1705, 1675,1600, 1545,1410, 1215,835, 775. | 229-30 (dec.) | C$_{13}$H$_9$N$_3$O$_4$ | 271.23 | 57.57 57.45 | 3.34 3.43 | 15.49 15.48 | — — |
| 3 | Br | Me | 1 | 68 | EtOAc | 3600–2300, 1715,1625, 1475,1200, 1110,1030, 775. | 164-5 (dec.) | C$_{13}$H$_{11}$BrN$_2$O$_4$ | 339.15 | 46.04 45.94 | 3.27 3.27 | 8.26 8.22 | Br 23.56 Br 23.47 |
| 4 | Cl | Me | 1 | 71 | EtOAc | 3600–2300, 1710,1635, 1450,1170, 1110,815, 685. | 165-6 (dec.) | C$_{13}$H$_{11}$ClN$_2$O$_4$ | 294.69 | 52.98 52.97 | 3.76 3.86 | 9.50 9.44 | Cl 12.03 Cl 11.95 |
| 5 | CF$_3$ | Me | 1 | 70 | EtOAc/P.E. (40°–60°) | 3600–2300, 1715,1625, 1595,1315, 1115,1040, 830. | 155-6 (dec.) | C$_{14}$H$_{11}$F$_3$N$_2$O$_4$ | 328.26 | 48.56 48.74 | 3.78 3.58 | 8.09 8.26 | F 16.46** F 16.47 |
| 6 | CN | Me | 1 | 53 | EtOAc | 3600–2300, 2220,1700, 1665,1600, 1550,1325, 1220,1120. | 232-3 (dec.) | C$_{14}$H$_{11}$N$_3$O$_4$ | 285.27 | 57.14 57.23 | 4.11 4.15 | 14.28 14.23 | —* — |
| 7 | SCF$_3$ | H | 2 | 97 | Et$_2$O/P.E. (40°–60°) | 3600–2400, 1720,1680, 1620,1135, 1110. | 158-9 (dec.) | C$_{13}$H$_9$F$_3$N$_2$O$_4$S | 346.28 | 43.95 44.08 | 2.84 2.85 | 7.88 7.88 | F 16.04 S 9.02* F 16.11 S 9.16 |
| 8 | OCF$_3$ | Me | 2 | 92 | Et$_2$O/P.E. (40°–60°) | 3600–2300, 3080,1720, 1630,1500, 1295,1205, 780. | 156-7 (dec.) | C$_{14}$H$_{11}$F$_3$N$_2$O$_5$ | 344.26 | 48.85 48.77 | 3.22 3.23 | 8.14 8.15 | F 16.56 F 16.47 |

Structure for Examples 9–12:

HO$_2$C—[isoxazole with N-O, cyclopropyl]—C(=O)—NH—C$_6$H$_3$(R$_4$)(R$_5$)

| Example | R4 | R5 | Synthetic Method | Yield (%) | Recryst. solvent | IR(KBr) $\nu_{max}$ cm$^{-1}$ | m.p. (°C.) | Formula | M.W. | C | H | N | X |
|---|---|---|---|---|---|---|---|---|---|---|---|---|---|
| 9 | CF$_3$ | H | 3 | 88 | Et$_2$O/P.E. (40°–60°) | 3600–2300, 1715,1635, 1600,1565, 1325,1120. | 160-1 (dec.) | C$_{15}$H$_{11}$F$_3$N$_2$O$_4$ | 340.27 | 52.95 52.96 | 3.26 3.32 | 8.23 8.25 | F 16.75 F 16.86 |
| 10 | CF$_3$ | Me | 3 | 94 | Et$_2$O/P.E. (40°–60°) | 3600–2300, 1715,1640, 1600,1565, 1310,1120, 1040. | 166-7 (dec.) | C$_{16}$H$_{13}$F$_3$N$_2$O$_4$ | 354.29 | 54.24 54.28 | 3.70 3.75 | 7.91 7.93 | F 16.09 F 16.20 |
| 11 | OCF$_3$ | H | 3 | 97 | Et$_2$O/P.E. (40°–60°) | 3600–2300, 1710,1675, 1630,1575, 1510,1255, 1155. | 141-2 (dec.) | C$_{15}$H$_{11}$F$_3$N$_2$O$_5$ | 356.27 | 50.57 50.50 | 3.11 3.10 | 7.86 7.83 | F 16.00 F 15.95 |
| 12 | SCF$_3$ | H | 3 | 98 | Et$_2$O/P.E. (40°–60°) | 3600–2300, 1720,1675, | 152-4 (dec.) | C$_{15}$H$_{11}$F$_3$N$_2$O$_4$S | 372.33 | 48.39 48.52 | 2.98 3.02 | 7.52 7.55 | F 15.31 S 8.61 F 15.24 S 8.66 |

TABLE I-continued

| Example | R4 | R5 | Synthetic Method | Yield (%) | Recryst. solvent | IR(KBr) $\nu_{max}$ cm$^{-1}$ | m.p. (°C.) | Formula | M.W. | C Calc/Found | H Calc/Found | N Calc/Found | X Calc/Found |
|---|---|---|---|---|---|---|---|---|---|---|---|---|---|
| 13 | OCF₃ | Me | 3 | 98 | Et₂O/P.E. (40°–60°) | 1625,1465, 1125,1015 765. 3600–2300, 3090,1720, 1640,1580, 1500,1460, 1260,1110. | 155–6 (dec.) | C₁₆H₁₃F₃N₂O₅ | 370.29 | 51.90 / 51.72 | 3.54 / 3.51 | 7.56 / 7.52 | F 15.39 / F 15.28 |

| Example | R4 | R5 | Synthetic Method | Yield (%) | Recryst. solvent | IR(KBr) $\nu_{max}$ cm$^{-1}$ | m.p. (°C.) | Formula | M.W. | C | H | N | X |
|---|---|---|---|---|---|---|---|---|---|---|---|---|---|
| 18 | CF₃ | Me | 1 | 81 | P.E. (40°–60°) | 3080,2980, 1705,1670, 1595,1305, 1210,1135, 1035,820. | 82–3 | C₁₆H₁₅F₃N₂O₄ | 356.31 | 53.94 / 53.90 | 4.24 / 4.26 | 7.86 / 7.89 | F 16.00 / F 16.15 |
| 14 | NO₂ | H | 1 | 76 | EtOAc | 3120,1700, 1670,1580, 1335,850. | 151–3 | C₁₄H₁₃N₃O₆ | 319.28 | 52.67 / 52.70 | 4.10 / 4.12 | 13.16 / 13.16 | — / — |
| 15 | CN | H | 1 | 67 | MeOH | 3100,2220, 1700,1670, 1595,1330, 840. | 175–7 | C₁₅H₁₃N₃O₄ | 299.29 | 60.20 / 60.15 | 4.38 / 4.40 | 14.04 / 14.07 | — / — |
| 16 | Br | Me | 1 | 89 | Et₂O/P.E. (40°–60°) | 3090,1700, 1665,1625, 1580,1470, 1210,1020 740. | 109–10 | C₁₅H₁₅BrN₂O₄ | 367.21 | 49.06 / 49.05 | 4.12 / 4.12 | 7.63 / 7.62 | Br 21.76 / Br 21.75 |
| 17 | Cl | Me | 1 | 89 | Et₂O/P.E. (40°–60°) | 3090,1700, 1665,1620, 1210,1025, 740. | 111–2 | C₁₅H₁₅ClN₂O₄ | 322.75 | 55.82 / 55.76 | 4.68 / 4.75 | 8.68 / 8.68 | Cl 10.98 / Cl 10.94 |
| 19 | CN | Me | 1 | 84 | Et₂O | 3110,2210, 1700,1675, 1605,1335, 1215,860. | 144–5 | C₁₆H₁₅N₃O₄ | 313.32 | 61.34 / 61.32 | 4.83 / 4.88 | 13.41 / 13.51 | — / — |
| 20 | SCF₃ | H | 2 | 74 | Et₂O/P.E. (40°–60°) | 3120,1710, 1680,1615, 1325,1210, 1135. | 117–8 | C₁₅H₁₃F₃N₂O₄S | 374.34 | 48.13 / 48.01 | 3.50 / 3.53 | 7.48 / 7.46 | F 15.23 S 8.56 / F 15.25 S 8.73 |
| 21 | OCF₃ | Me | 2 | 80 | P.E. (40°–60°) | 3110,1715, 1675,1625, 1500,1265, 1160,872. | 63–5 | C₁₆H₁₅F₃N₂O₅ | 372.31 | 51.62 / 51.51 | 4.06 / 4.06 | 7.52 / 7.49 | F 15.31 / F 15.19 |

| Example | R4 | R5 | Synthetic Method | Yield (%) | Recryst. solvent | IR(KBr) $\nu_{max}$ cm$^{-1}$ | m.p. (°C.) | Formula | M.W. | C | H | N | X |
|---|---|---|---|---|---|---|---|---|---|---|---|---|---|
| 22 | CF₃ | H | 3 | 68 | P.E. (40°–60°) | 3090,1710, 1670,1605, 1325,1110, 845. | 100–1 | C₁₇H₁₅F₃N₂O₄ | 368.32 | 55.44 / 55.47 | 4.11 / 4.15 | 7.60 / 7.62 | F 15.48 / F 15.55 |
| 23 | CF₃ | Me | 3 | 70 | P.E. (40°–60°) | 3110,1710, 1675,1615, 1550,1310, 1105. | 99–100 | C₁₈H₁₇F₃N₂O₄ | 382.35 | 56.55 / 56.48 | 4.48 / 4.53 | 7.33 / 7.31 | F 14.91 / F 14.93 |
| 24 | OCF₃ | H | 3 | 65 | P.E. (40°–60°) | 3100,1700, 1670,1625, 1570,1505, 1275,1210. | 87–8 | C₁₇H₁₅F₃N₂O₅ | 384.32 | 53.13 / 53.24 | 3.93 / 3.98 | 7.29 / 7.34 | F 14.83 / F 14.94 |
| 25 | SCF₃ | H | 3 | 55 | P.E. (40°–60°) | 3130,1715 1685,1635, | 151–2 | C₁₇H₁₅F₃N₂O₄S | 400.38 | 51.00 / 50.96 | 3.78 / 3.81 | 7.00 / 7.06 | F 14.24 S 8.01 / F 14.28 S 8.15 |

TABLE I-continued

| Example | R₄ | R₅ | Synthetic Method | Yield (%) | Recryst. solvent | IR(KBr) $\nu_{max}$ cm$^{-1}$ | m.p. (°C.) | Formula | M.W. | ANALYSIS Calculated/Found C | H | N | X |
|---|---|---|---|---|---|---|---|---|---|---|---|---|---|
| 26 | OCF₃ | Me | 3 | 73 | P.E. (40°–60°) | 1580,1125, 840. 3110,1710 1670,1570, 1397,1255, 1155,1095. 1020,760. | 84–5 | $C_{18}H_{17}F_3N_2O_5$ | 398.35 | 54.27 54.18 | 4.30 4.30 | 7.03 7.00 | F 14.31 F 14.28 |

*hemihydrate
**monohydrate

Synthetic Method 1 is schematically shown as follows for Example 1:

Synthetic Method 2 is schematically shown as follows for Example 7:

Synthetic Method 3 is schematically shown as follows for Example 9:

PHARMACOKINETIC DATA

Figure 1A:
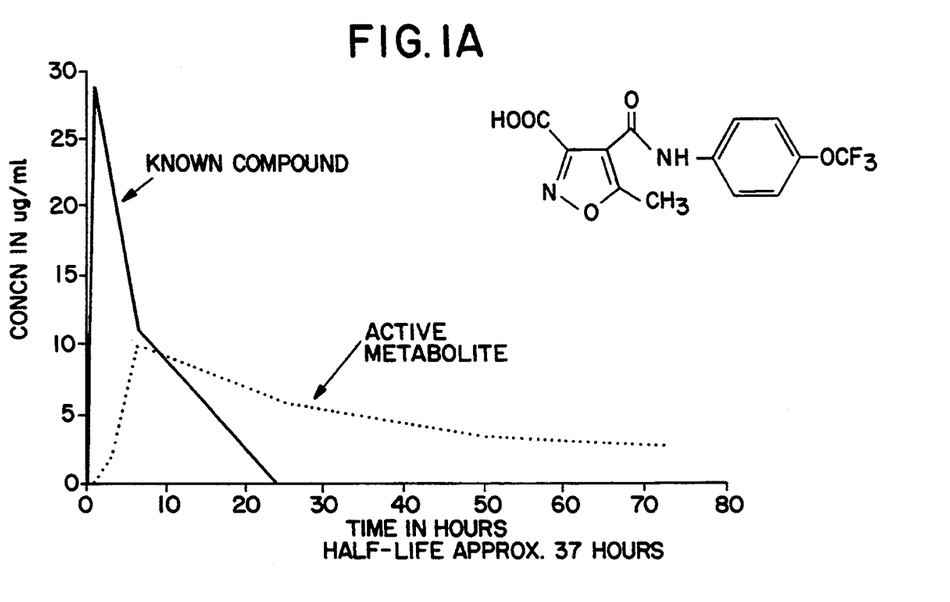
Figure 1B:
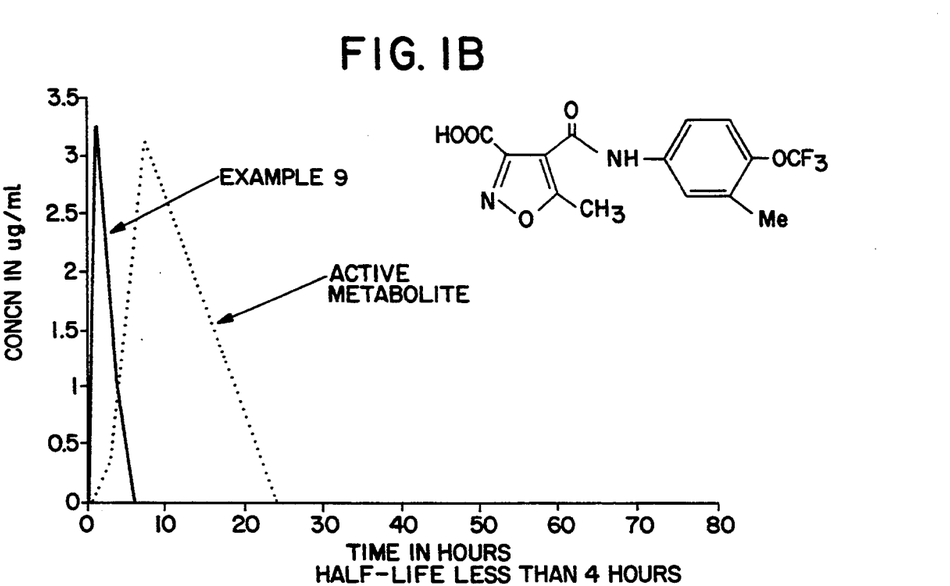

A pharmacokinetic comparison was made between the compound of Example 8 in which $R_5$ is methyl and the corresponding known compound in which $R_5$ is hydrogen. Each compound was administered orally to mice at a dose of 30 mg/kg and plasma concentrations of the parent compound and the corresponding active metabolite were determined at various time points after administration. The results are shown in FIG. 1. The results show that the half-life of the active metabolite of the known compound is in the region of 37 hours, with the metabolite still being detectable at 72 hours after administration. In contrast, the compound of Example 8 forms an active metabolite with a half life of less than 4 hours, with no metabolite detectable 24 hours after administration. Thus, the presence of the methyl substituent in the compound of Example 9 clearly leads to improved pharmacokinetics.

PHARMACOLOGICAL ACTIVITY

Biochemical Test Methods

Test 1
Carrageenan rat paw oedema (PO-R)

One hour after the oral administration of the test compounds or control vehicle to groups of 6 to 12 male CFHB rats, weighing 160–180 g, 1 mg of carrageenan dissolved in 0.2 ml of saline was injected into the right hind foot pad. Contralateral paws received control saline injections. Paw oedema responses were assessed three hours later.

Test 2
Delayed-type hypersensitivity mouse paw oedema (DTH-M)

Groups of 8 to 10 mice, male CD-1 weighing 25–30 g were sensitized by the subcutaneous injection of 1 mg of methylated bovine serum albumin (MBSA) in 0.2 ml volumes of saline/Freund's complete adjuvant (FCA) emulsion. Negative control groups received injections of saline/FCA emulsion. DTH paw oedema responses were assessed twenty-four hours after the right hind foot pad challenge with 0.1 mg of MBSA in 0.05 ml volumes of saline on day seven after sensitization. Contralateral paws received control saline injections. The test compounds or control vehicles were orally administered daily on days four, five, six and twice on day seven, one hour before and six hours after MBSA challenge.

Test 3
Delayed-type hypersensitivity rat paw oedema (DTH-R)

Groups of 8 to 12 male CFHB rats, weighing range 160–180 g, were sensitised by the subcutaneous tail base injection with 0.1 ml volumes of FCA. Negative control groups received an injection of Freund's incomplete adjuvant. DTH paw oedema responses were assessed twenty-four hours after the right hind foot pad challenge with 0.4 mg of Mycobacterium tuberculosis extract antigen in 0.2 volumes of saline on day seven after sensitisation. Contralateral paws received control saline injections. The test compounds were orally administered daily on days fours, five, six and twice on day seven, one hour before and six hours after antigenic challenge.

The results of these tests are given in Table II.
Doses are given in units of mg/kg p.o.

TABLE II

| Example | Test 1 % Inhibition | Dose | Test 2 % Inhibition | Dose | Test 3 % Inhibition | Dose |
| --- | --- | --- | --- | --- | --- | --- |
| 1 | −2 | 50 | 41 | 100 | 28 | 50 |
| 2 | −25 | 50 | 27 | 100 | −47 | 50 |
| 3 | −10 | 50 | 35 | 100 | −4 | 50 |
| 4 | −10 | 50 | 24 | 100 | 6 | 50 |
| 5 | 18 | 50 | 44 | 100 | 95 | 50 |
|   |    |    |    |     | 44 | 10 |
| 6 | 5 | 50 | 5 | 100 | 25 | 50 |
| 7 | 1 | 50 | 14 | 100 | 73 | 50 |
|   |    |    |    |     | 42 | 10 |
| 8 | 16 | 10 | 48 | 100 | 79 | 50 |
|   |    |    |    |     | 34 | 10 |
| 9 | −24 | 10 | 72 | 100 | 86 | 50 |
|   |    |    |    |     | 45 | 10 |
| 10 | 5 | 50 | 12 | 100 | 73 | 50 |
| 11 | −2 | 3 | 65 | 100 | Toxic | 50 |
|    |    |   | 37 | 30 | 95 | 10 |
|    |    |   |    |    | 65 | 3 |
| 12 | 11 | 10 | 36 | 100 | 75 | 10 |
| 13 | 5 | 10 | 52 | 100 | 47 | 10 |
| 18 | 23 | 50 | 3 | 100 | 50 | 50 |

Various modifications of the compounds and method of the invention may be made without departing from the spirit or scope thereof and it is to be understood that the invention is intended to be limited only as defined in the appended claims.

What is claimed is:

1. A compound selected from the group consisting of a compound of the formula wherein $R_1$ is hydrogen or alkyl of 1 to 3 carbon atoms, $R_2$ is alkyl of 1 to 3 carbon atoms or cycloalkyl of 3 to 6 carbon atoms, $R_3$ is —COOR$_6$, $R_6$ is hydrogen or alkyl of 1 to 3 carbon atoms, $R_4$ is selected from the group consisting of halogen, —CN, —NO$_2$, —CX$_3$, —WCX$_3$, X is halogen, W is —O— or —S—, n is 1 , 2 or 3, $R_5$ is selected from the group consisting of alkyl of 1 to 3 carbon atoms and cycloalkyl of 3 to 6 carbon atoms and their salts with non-toxic pharmaceutically acceptable bases.

2. A compound of claim 1 wherein $R_1$ is hydrogen, $R_2$ is methyl or cyclopropyl, $R_4$ is selected from the group consisting of halogen, —NO$_2$, —CN, —CF$_3$, —OCF$_3$ and —SCF$_3$ and $R_5$ is selected from the group consisting of methyl, ethyl and cyclopropyl.

3. A compound of claim 1 wherein $R_4$ is selected from the group consisting of —CF$_3$, —OCF$_3$ and —SCF$_3$ and $R_5$ is methyl.

4. A compound of claim 1 selected from the group consisting of:
5-methyl-4-[N-(3-methyl-4-trifluoromethyl)phenyl]carbamoyl-3-isoxazolecarboxylic acid;
5-methyl-4-[N-(4-trifluoromethylthio)phenyl]carbamoyl-3-isoxazolecarboxylic acid;
5-methyl-4-[N-(3-methyl-4-trifluoromethoxy)phenyl]carbamoyl-3-isoxazolecarboxylic acid;
5-cyclopropyl-4-[N-(3-methyl-4-trifluoromethoxy)phenyl]carbamoyl-3-isoxazolecarboxylic acid; and their salts with non-toxic, pharmaceutically acceptable bases.

5. An antiinflammatory composition comprising an antiinflammatarily effective amount of at least one compound of claim 1 and a pharmaceutical carrier.

6. A composition of claim 5 wherein $R_1$ is hydrogen, $R_2$ is methyl or cyclopropyl, $R_4$ is selected from the group consisting of halogen, —NO$_2$, —CN, —CF$_3$, —OCF$_3$ and —SCF$_3$ and $R_5$ is selected from the group consisting of methyl, ethyl and cyclopropyl.

7. A composition of claim 5 wherein the active compound is selected from the group consisting of a compound of the formula
5-methyl-4-[N-(3-methyl-4-trifluoromethyl)phenyl]carbamoyl-3-isoxazolecarboxylic acid;
5-methyl-4-[N-(4-trifluoromethylthio)phenyl]carbamoyl-3-isoxazolecarboxylic acid;
5-methyl-4-[N-(3-methyl-4-trifluoromethoxy)phenyl]carbamoyl-3-isoxazolecarboxylic acid;
5-cyclopropyl-4-[N-(3-methyl-4-trifluoromethoxy)phenyl]carbamoyl-3-isoxazolecarboxylic acid; and their salts with non-toxic, pharmaceutically acceptable bases.

8. A method of treating inflammation in warm-blooded animals comprising administering to warm-blooded animals an antiinflammatorily effective amount of at least one compound of claim 1.

9. A method of claim 8 wherein $R_1$ is hydrogen, $R_2$ is methyl or cyclopropyl, $R_4$ is selected from the group consisting of halogen, —NO$_2$, —CN, —CF$_3$, —OCF$_3$ and —SCF$_3$ and $R_5$ is selected from the group consisting of methyl, ethyl and cyclopropyl.

10. A method of claim 8 wherein $R_4$ is selected from the group consisting of —CF$_3$, —OCF$_3$ and SCF$_3$ and $R_5$ is methyl.

11. A method of claim 8 wherein the active compound is selected from the group consisting of a compound of the
5-methyl-4-[N-(3-methyl-4-trifluoromethyl)phenyl]carbamoyl-3-isoxazolecarboxylic acid;
5-methyl-4-[N-(4-trifluoromethylthio)phenyl]carbamoyl-3-isoxazolecarboxylic acid;
5-methyl-4-[N-(3-methyl-4-trifluoromethoxy)phenyl]carbamoyl-3-isoxazolecarboxylic acid;
5-cyclopropyl-4-[N-(3-methyl-4-trifluoromethoxy)phenyl]carbamoyl-3-isoxazolecarboxylic acid; and their salts with non-toxic, pharmaceutically acceptable bases.

12. A compound of claim 1 wherein $R_5$ is alkyl of 1 to 3 carbon atoms.

* * * * *